Dec. 13, 1955 C. TEMMERMAN Plant Pat. 1,436
ROSE PLANT
Filed Dec. 28, 1954
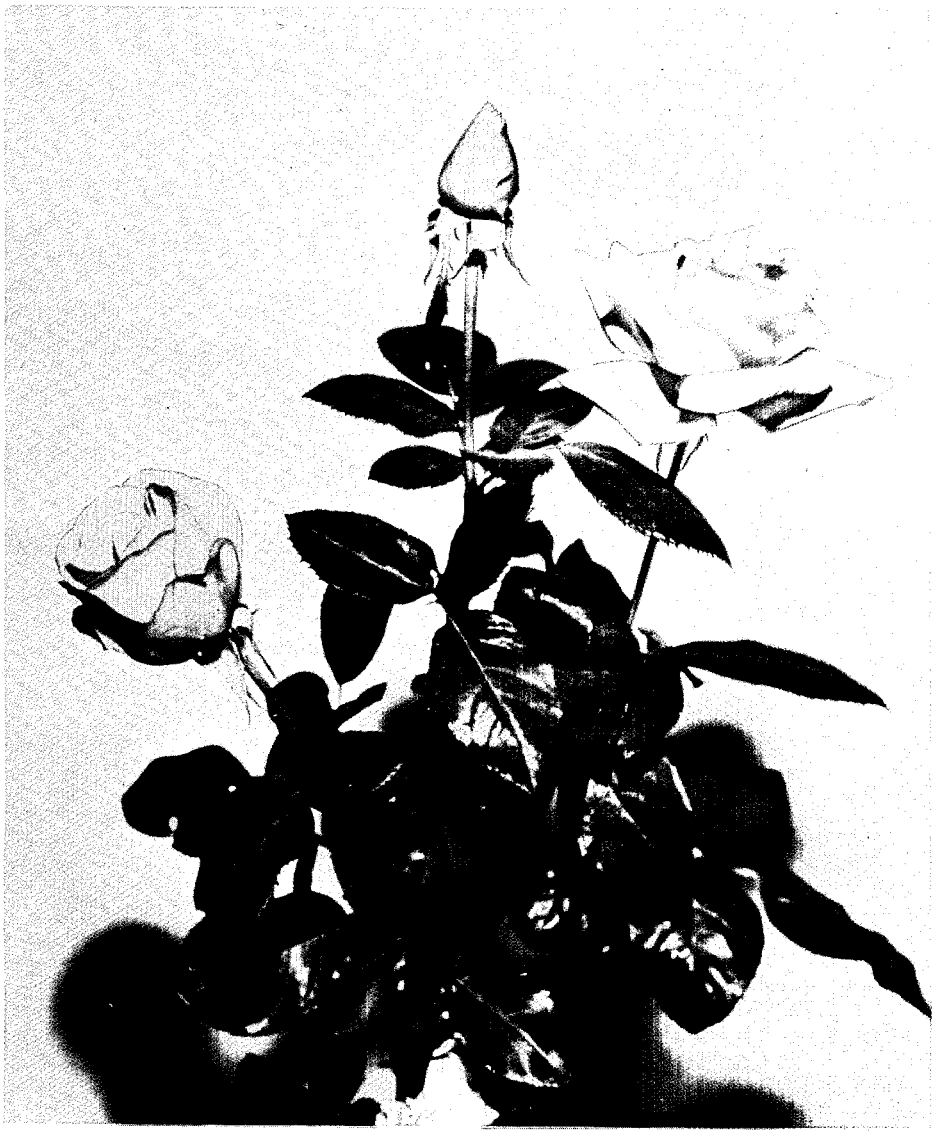
Inventor.
Clement Temmerman
By: Robb & Robb
Attorneys United States Patent Office Plant Pat. 1,436
Patented Dec. 13, 1955

1,436

ROSE PLANT

Clement Temmerman, Serskamp, Belgium, assignor, by mesne assignments, to McHutchison & Co., New York, N. Y., a corporation of New Jersey, and Floral Avenue Greenhouse Company, Mount Clemens, Mich., a corporation of Illinois Application December 28, 1954, Serial No. 478,222

1 Claim. (Cl. 47—61)

The present invention relates to a new and distinct variety of rose plant of the hybrid tea class, which was originated by me by crossing the variety "Ena Harkness" (unpatented) with the variety "Hens Verschuren" (unpatented).

As the result of this breeding, I have produced a new variety of rose plant which is particularly distinguished from its parents, as well as from all other varieties of its class of which I am aware, by the following outstanding characteristics:

(1) The uniform deep Red general color tonality throughout of the blooms, and their almost Black color when in the bud stage;

(2) The large size and the perfect shape of the buds, and the ideal shape of the open flowers;

(3) The long, strong and healthy shoots and stems on which the flowers are borne, as are especially desirable for cut flowers;

(4) The slow-opening habit and the long-lasting and color-retaining qualities of the flowers as cut flowers;

(5) The relatively large size of the flower petals, producing a heavy flower whose appearance belies the small petalage count;

(6) The unusual ability of the flowers to develop in size and color while kept under cold storage conditions at a temperature of approximately 40°;

(7) The good keeping qualities of the flowers under cold storage conditions; and (8) The vigorous and strong habits of growth of the plant, and its healthy foliage.

Asexual reproduction of my new variety by both budding and grafting, as performed by me at Serskamp, Belgium, and on my behalf at Mount Clemens, Michigan, U. S. A., shows that the foregoing characteristics and distinctions come true to form and are established and transmitted through succeeding propagations.

The accompanying drawing shows typical specimens of the buds, flowers, foliage and stems of my new variety in different stages of development and as depicted in color as nearly true as it is reasonably possible to make the same in a color illustration of this character.

The following is a detailed description of my new variety, with color terminology in accordance with Koster's Color Guide, except where general color terms of ordinary dictionary significance are obvious:

Type: Hardy; bush; greenhouse; seedling; for cut flowers.
Class: Hybrid tea.
Breeding: Seedling.
*Seed parent.*—"Ena Harkness."
*Pollen parent.*—"Hens Verschuren."
Propagation: Holds its distinguishing characteristics through succeeding propagations by both budding and grafting.

FLOWER

Locality where grown and observed: Mount Clemens, Michigan, U. S. A. and Serskamp, Belgium.
Continuity: Continuous.

Fragrance: Slight.
Flowers borne: Singly; on strong, long stems.
Quantity of bloom: Free, in greenhouse.
Bud:
*Peduncle.*—Medium length; medium caliper; stiff; almost smooth; with few yellow prickles. Color—Moss Green, Plate 76.
*Before calyx breaks.* — Size — medium. Form—Pointed; without foliaceous appendages on the surface of the bud; with slender, much-cut, bristle-like foliaceous parts extending beyond the tip of the bud equal to ¼ or more of its length. Color—Moss Green, Plate 76.
*As calyx breaks.*—Color—Deep Purple, Plate 52.
*As first petal opens.*—Size—large. Form—long; ovoid. Color: outside—Crimson Carmine, Plate 41; inside—Ox Blood Red, Plate 25.
*Opening.*—Opens up well.
Bloom:
*Size (when fully open).*—From 4½ inches to 6 inches.
*Petalage.*—Double; from 20 to 25 petals; arranged irregularly.
*Form.*—Ovate at first, but becoming cupped; petals at first being tightly rolled inward, but becoming very loosely cupped later at maturity.
Petals:
*Texture.* — Leathery. Inside — velvety; outside—satiny.
*Shape.*—Outside—obovate; scalloped; with apex flat; usually with 1 notch. Intermediate—obovate; scalloped; with apex flat; usually with 1 notch. Inside—obovate; with apex flat; usually with 1 notch.

This description of a newly opened flower was made from a rose grown in a greenhouse in the month of September, at Mount Clemens, Michigan, U. S. A.:

*Color.*—Outside petal: outside surface—Crimson Carmine, Plate 41; inside surface—Ox Blood Red, Plate 25. Intermediate petal: outside surface—Rosy Magenta, Plate 44; inside surface—Crimson Carmine, Plate 41. Inner petal: outside surface—Ox Blood Red, Plate 25; inside surface—Ox Blood Red, Plate 25.

This description was made from a rose that was open for 3 days in a greenhouse in the month of September, at Mount Clemens, Michigan, U. S. A.:

*Color.*—Outside petal: outside surface—Crimson Carmine, Plate 41; inside surface—Ox Blood Red, Plate 25. Inside petal: outside surface—Crimson Carmine, Plate 41; inside surface—Ox Blood Red, Plate 25.
*General color effect.*—Newly opened flower—Ox Blood Red, Plate 25. 3-days open—Ox Blood Red, Plate 25, with tint of Crimson Carmine, Plate 41.
*Behavior.*—Persist; only slight fading to Purple.
*Flower longevity.*—Cut roses grown in greenhouse and kept at living-room temperatures—5 or 6 days in September.

REPRODUCTIVE ORGANS

Stamens: Many; arranged regularly about pistils.
Filaments: Medium length; most with anthers.
*Color.*—Ox Blood Red, Plate 25.
Anthers: Medium size; all open at once.
*Color.*—Rosy Pink, Plate 33.
Pollen: Abundant.
*Color.*—Sulphur Yellow, Plate 5.
Pistils: Many.

Styles: Uneven; medium length; medium weight; bunched.
Stigma:
*Color.*—Sulphur Yellow, Plate 5.
Ovaries: All enclosed in calyx.
Hips: None observed.
Sepals: Permanent; moderate length; recurved.
*Color.*—Moss Green, Plate 76.
Seeds: None observed.

PLANT

Foliage:
*Leaves.*—Compound of 3–5–7 leaflets; moderately abundant; medium large; moderately thin; soft.
*Leaflets.*—Shape—oval; apex—acute; base—round; margin—doubly serrate.
*Color.*—Mature: upper surface—Ivy Green, Plate 83; under surface—Apple Green, Plate 77. Young: upper surface—near Amaranth Red, Plate 43; under surface—near Amaranth Red, Plate 43.
*Rachis (the supporting stem of the compound leaf).*—Medium weight. Upper side—grooved; under side—sparsely prickly.
*Stipules.*—Very short; moderately wide; with very short points turning out at an angle of approximately 45°.
*Disease resistance.*—Slightly subject to mildew, as determined by comparison with other varieties grown under comparable cultural conditions at Mount Clemens, Michigan, U. S. A.
Growth:
*Habit.*—Bushy; upright; little-branched.
*Growth.*—Moderately vigorous.

*Canes.*—Heavy.
*Main stems.*—Color—Moss Green, Plate 76. Thorns—many; long; some straight and some hooked downward; with oval base. Prickles—many. Color—brown. Hairs—none.
*Branches.*—Color—Moss Green, Plate 76. Thorns—many; medium length; some straight and some hooked downward; with oval base. Prickles—many; color—brown. Hairs—none.
*New shoots.*—Color—near Amaranth Red, Plate 43. Thorns—very many; long; some straight and some hooked downward; with oval base. Prickles—many; color—near Amaranth Red, Plate 43. Hairs—few; translucent.

I claim:

A new and distinct variety of rose plant of the hybrid tea class, substantially as herein shown and described, characterized particularly as to novelty by the uniform red general color tonality of the blooms and their almost black color when in the bud stage, the large size and the perfect shape of the buds and the ideal shape of the open flowers, the long, strong and healthy shoots and stems on which the flowers are borne, the slow-opening habit and the long-lasting and color-retaining qualities of the flowers as cut flowers, the relatively large size of the flower petals, the good keeping qualities and the unusual ability of the flowers to develop in size and color when kept under cold storage conditions, and the vigorous and strong habits of growth of the plant and its healthy foliage.

No references cited.